(12) United States Patent
Wang et al.

(10) Patent No.: US 10,611,745 B2
(45) Date of Patent: Apr. 7, 2020

(54) PROCESS FOR PREPARING 5-PHENOXY-1(3)ISOBENZOFURANONE

(71) Applicant: KINGCHEM LIFE SCIENCE LLC, Allendale, NJ (US)

(72) Inventors: Zheqing Wang, Allendale, NJ (US); Lillian Wu, Allendale Park, NJ (US); Yang Zhao, Allendale, NJ (US); Zhenwei Li, Allendale, NJ (US)

(73) Assignee: KINGCHEM LIFE SCIENCE LLC, Allendale, NJ (US)

( * ) Notice: Subject to any disclaimer, the term of this patent is extended or adjusted under 35 U.S.C. 154(b) by 0 days.

(21) Appl. No.: 16/370,595

(22) Filed: Mar. 29, 2019

(65) Prior Publication Data
US 2019/0225591 A1    Jul. 25, 2019

Related U.S. Application Data

(63) Continuation-in-part of application No. PCT/US2017/068185, filed on Dec. 22, 2017.

(60) Provisional application No. 62/451,690, filed on Jan. 28, 2017.

(51) Int. Cl.
*C07D 209/48* (2006.01)
*C07D 307/88* (2006.01)

(52) U.S. Cl.
CPC ......... *C07D 307/88* (2013.01); *C07D 209/48* (2013.01); *Y02P 20/582* (2015.11)

(58) Field of Classification Search
CPC ............................ C07D 209/48; C07D 307/88
See application file for complete search history.

(56) References Cited

PUBLICATIONS

Williams et al., Journal of Organic Chemistry, vol. 42, 1977, 3414-3419.*
Francis et al., Canadian Journal of Chemistry, vol. 57, 1979, 3320-3331.*

* cited by examiner

*Primary Examiner* — Sun Jae Yoo
(74) *Attorney, Agent, or Firm* — Kurt T. Mulville; VLP Law Group, LLP

(57) ABSTRACT

The disclosure provides a simple and efficient method for producing a compound of Formula I. The method includes treating an N-substituted-4-nitro-phthalimide of Formula VII with sodium or potassium phenoxide to form an N-substituted-4-phenoxy-phthalimide of Formula VIII and then treating the N-substituted-4-phenoxy-phthalimide of Formula VIII with, for example zinc, in the presence of a base to give 5-phenoxy-1(3H)-isobenzofuranone of Formula I, its isomer of 6-phenoxy-1 (3H)-isobenzofuranone of Formula Ia, and alkyl amine or aryl amine $NH_2R$ (Formula IX)

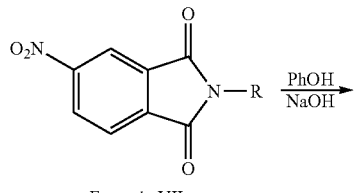

Formula VII

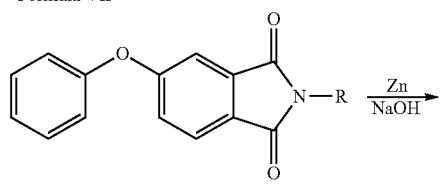

Formula VIII

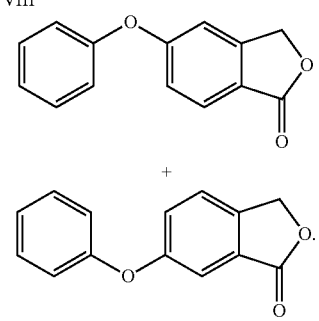

Formula I (top) and Ia (bottom)

15 Claims, No Drawings

PROCESS FOR PREPARING 5-PHENOXY-1(3)ISOBENZOFURANONE

CROSS REFERENCE TO RELATED APPLICATION

This application is a Continuation-In-Part of International Patent Application PCT/US20107/068185, filed Dec. 22, 2017, which claims priority of U.S. Provisional Application No. 62/451,690, filed Jan. 28, 2017, both of which are hereby incorporated by reference in their entirety.

FIELD OF THE DISCLOSURE

The disclosure provides a process for the preparation of 5-phenoxy-1(3H)-isobenzofuranone, Formula (I):

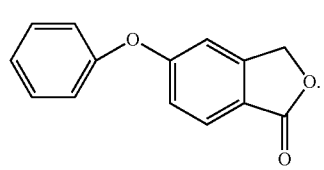

(Formula I)

BACKGROUND

5-Phenoxy-1(3H)-isobenzofuranone is a useful intermediate in the preparation of the derivatives of isoquinoline. Example 3 of WO 2014014834 A1 discloses a method for its preparation:

Scheme I

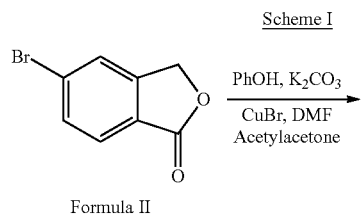

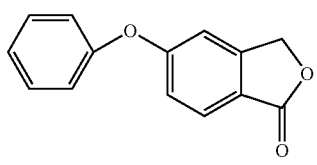

Formula I

The reaction follows Ullmann diaryl ether synthesis conditions and gives a fair yield of 72%. This method uses a large amount of copper bromide, which is carried as heavy metal waste into the waste system.

Example 1 of WO 2013134660 A1 provides a method of preparing a compound of Formula I from a compound of Formula II, in which CuCl, 2,2,6,6-tetramethyl-heptane-3,5-dione (TMHD), and expensive cesium carbonate are used as reactants and reagents. Furthermore, the industrial process required to produce 5-bromo-1(3H)isobenzofuranone (Formula II) is a long and complicated process.

Scheme II

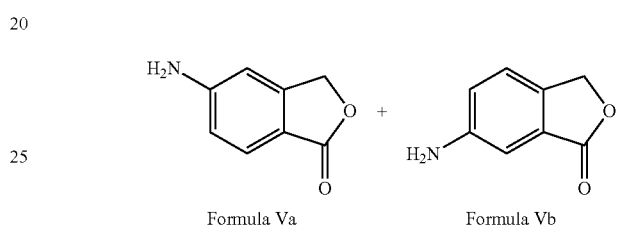

The process for preparing the intermediate of Formula II has several obvious disadvantages, including (1) the requirement for four reaction steps, (2) generation of a large amount of heavy metal waste, (3) performing a diazotatization reaction that generates a potentially unstable diazonium salt, and (4) the difficulty of separating the desired 5-amino-1(3H)isobenzofuranone of Formula Va from its 6-isomer of Formula Vb. This process is widely discussed in the scientific literature and published patents, see for Example WO 2006/103550 A1.

Chem. Pharm. Bull. (1978) 26(2): 530-538 describes a method for preparing 5-nitro-1(3H)isobenzofuranone of Formula XIII from which 5-bromo-1(3H)isobenzofuranone of Formula II can be prepared following the same sequence of reduction, diazotation and bromo-replacement set forth in Scheme II. But, the $NaBH_4$-reduction only gives 21% of the desired product of Formula XIII.

Scheme III

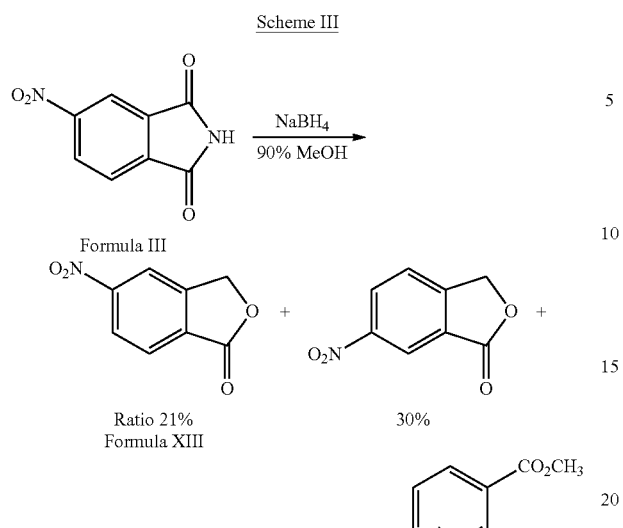

Therefore, there is a need for a green and economically favorable process for producing 5-phenoxy-1(3H)-isobenzofuranone. The desired process has fewer steps, produces less waste, recycles chemical reactants, and provides high regioselectivity during the reduction to form the lactone.

SUMMARY

In one aspect the disclosure provides a process for preparing 5-phenoxy-1(3H)-isobenzofuranone of Formula I. The process is shown in Scheme IV:

Formula I

The process provided by this disclosure has only two steps: (1) treating N-substituted-4-nitro-phthalimide of Formula VII with sodium phenoxide to form N-substituted-4-phenoxy-phthalimide of Formula VIII; and (2) treating Formula VIII with zinc in the presence of a base. Although zinc is the preferred compound for step 2 and is used as the reducing compound in the following working examples and specific embodiments, iron powder, granulated iron, tin powder, granulated tin, a combination of iron powder and ferrous sulfate, a combination of tin powder and stannous chloride, and combinations thereof may also be used.

In another aspect the disclosure provides a method of producing the product, a compound of Formula I, with regioselectivity during the reduction with zinc or the aforementioned compounds to form the lactone product, for the compound of Formula I over its isomer, the compound of Formula Ia.

In another aspect the disclosure provides a simple and effective purifying method for separating 5-phenoxy-1(3H)-isobenzofuranone (Formula I) from its isomer 6-phenoxy-1(3H)-isobenzofuranone (Formula Ia) by recrystallization or slurry in solvent.

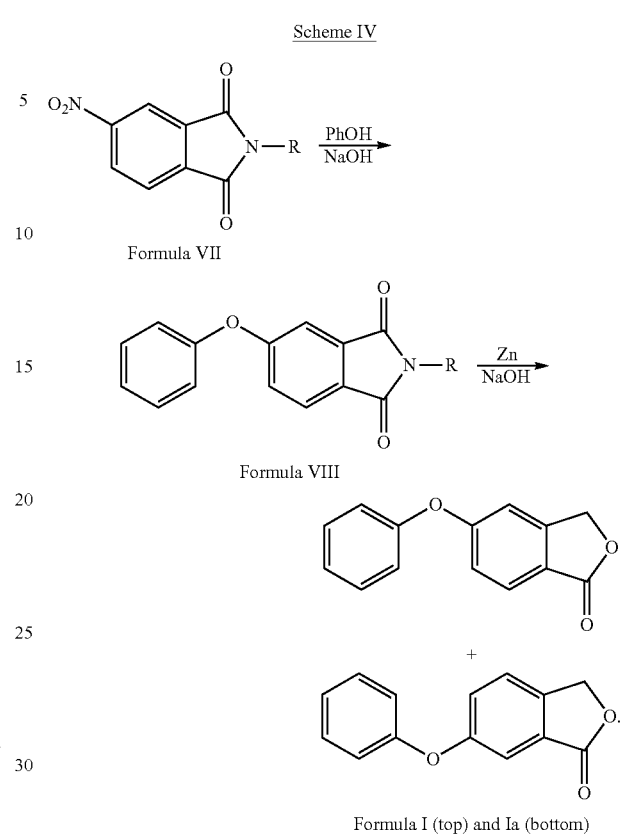

In Scheme IV R is an alkyl or aryl group.

In yet another aspect the disclosure provides the green chemistry process shown in Scheme V. In the Scheme V process the substituted amines of Formula IX generated during the second step of reduction with zinc (or the aforementioned compounds) can be reused as one of the starting materials to prepare the intermediate of Formula VII

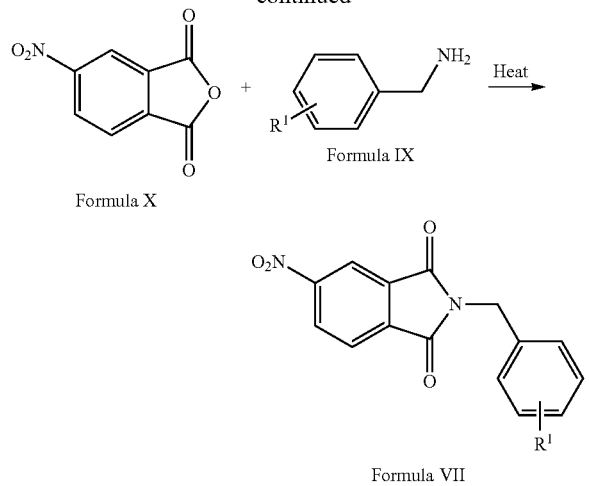

Within Scheme V, $R^1$ can be H, Cl, Br, F, $NO_2$, CN, $C_1$-$C_6$alkoxy such as —$OCH_3$ or —$OC_2H_5$, or $C_1C_6$alkyl, such as —$CH_3$, —$C_2H_5$, propyl, isopropyl, n-butyl, or t-butyl.

DETAILED DESCRIPTION OF THE INVENTION

Terminology

In the specification and claims that follow, references will be made to a number of terms which shall be defined to have the following meaning.

The terms "a" and "an" do not denote a limitation of quantity, but rather denote the presence of at least one of the referenced item. The term "or" means "and/or".

The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to for illustration and does not pose a limitation on the scope of the disclosure unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this disclosure belongs.

The term "substituted," as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, e.g., halogen; cyano; —OH; oxo; —$NH_2$; nitro; azido; alkanoyl (such as a $C_2$-$C_6$ alkanoyl group); $C(O)NH_2$; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; mono- or dialkylamino groups including groups having alkyl groups from 1 to about 6 carbon atoms; mono- or dialkylcarboxamido groups (i.e. alkylNHC(O)—, $(alkyl_1)(alkyl_2)NC(O)$—, alkylC(O)NH—, or $alkyl_1C(O)N(alkyl_2)$-) having alkyl groups from about 1 to about 6 carbon atoms. In certain embodiments "substituted" or "optionally substituted" includes one or more substituents independently chosen from halogen, hydroxyl, amino, cyano, CHO, —$CO_2H$, —$C(O)NH_2$, $C_1$-$C_6$-alkyl, $C_2$-$C_6$-alkenyl, $C_1$-$C_6$-alkoxy, $C_2$-$C_6$-alkanoyl, $C_1$-$C_6$-alkylester, (mono- and di-$C_1$-$C_6$-alkylamino)$C_0$-$C_2$-alkyl, (mono- and di-$C_1$-$C_6$-alkylamino)(CO)$C_0$-$C_2$-alkyl, $C_1$-$C_2$-haloalkyl, and $C_1$-$C_2$haloalkoxy. In certain embodiments "substituted" or "optionally substituted" includes halogen, hydroxyl, cyano, nitro, —$CONH_2$, amino, $C_1$-$C_6$alkyl (in which a —$CH_2$— group may be replaced by —O—, —S—, —NH—, or —N($C_1$-$C_6$alkyl)-), $C_1$-$C_2$haloalkyl, or $C_1$-$C_2$haloalkoxy.

"Alkyl" is a branched or straight chain saturated aliphatic hydrocarbon group, having the specified number of carbon atoms, generally from 1 to about 8 carbon atoms. The term $C_1$-$C_6$-alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$-alkyl, $C_1$-$C_4$-alkyl, and $C_1$-$C_2$-alkyl. Examples of alkyl include, but are not limited to, methyl, ethyl, n-propyl, isopropyl, n-butyl, 3-methylbutyl, t-butyl, n-pentyl, and sec-pentyl.

"Aryl" is an aromatic group containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Aryl groups include, for example, phenyl and naphthyl, including 1-naphthyl and 2-naphthyl. When a group "aryl($C_0$-$C_2$alkyl)" is specified the point of attachment of the aryl($C_0$-$C_2$alkyl) to the group it substitutes is on the alkyl, or in the case of $C_0$alkyl, the point of attachment is a single covalent bond to the aryl. "Aryl($C_0$-$C_2$alkyl) groups include but are not limited to phenyl, benzyl, and phenylethyl.

Compounds of this disclosure can have isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$. In some embodiments, any one or more hydrogen atoms are replaced with deuterium atoms.

Chemical Description

The disclosure provides a simple and efficient process for the preparation of 5-Phenoxy-1(3H)-isobenzofuranone of Formula I. The process design is based upon the following five concepts:
1. The phthalimide ring (Formula VII) has a much stronger electron-withdrawing potency than the lactone ring (Formula II) has to activate a nitro or halo substituent at position 3 or 4. Therefore, the diaryl ether formation should be performed prior to the reduction.
2. The nitro group attached at position 3 or 4 of Formula II is a stronger leaving group than any halogen group, —F, —Cl, —Br— or —I.
3. The bulky phenoxy-group bound at position 4 of the phthalimide ring of Formula VIII causes the reduction step using zinc, or the compounds described above, to be favorable, producing more of the desired product of Formula I.
4. A simple and low cost method should be applied to purify the desired product. Such methods include recrystallization, slurry, or a combination of both.
5. The whole process should meet the standards of green chemistry, such as, but not limited to, the elimination of heavy metal reagents, and the recycling of reagents used in the process, such as alkylamine, substituted phenylamine, and substituted benzylamine.

The following details should be considered when viewing Scheme IV. Anhydrous sodium phenoxide is needed for the formation of the diarylether intermediate (Formula VIII). Previous methods for the preparation of sodium phenoxide compounds were hazardous or commercially impractical due to the use of sodium metal or sodium methoxide. For example, Williams and Donahue (*J. Org. Chem.* (1977) 42 (21): 3414-3419) described the reactions of phenoxides with nitro- and halo-substituted phthalimides.

The disclosure provides a simple method to finish two reactions, the formation of sodium phenoxide and subsequent production of the diaryl ether intermediate (Formula VIII), in one pot using low cost commercial grade sodium hydroxide aqueous solution in place of sodium metal and sodium methoxide.

To form anhydrous sodium phenoxide, aqueous Sodium hydroxide solution, phenol and toluene are mixed in a flask, heated to reflux for 30-90 minutes, and then dehydrated by azeotropic distillation to remove water from the system. DMSO is added to make a solvent exchange. The temperature is kept at 90-120° C. till all toluene is distilled away. Anhydrous sodium phenoxide thus forms and can be used for the ether formation in the same reaction vessel without isolation. The remaining DMSO is used as a solvent for the diaryl ether formation during next step. The same method can be used to form anhydrous potassium phenoxide.

After formation of sodium phenoxide the reaction mixture is cooled to 40-60° C. 4-Nitro-N-substituted phthalimide of Formula VII is added, and continuously kept running at 40-80° C. for 4-10 hours.

The reaction mixture is then heated and concentrated to remove most of the DMSO, then cooled to 10-30° C. The mixture is adjusted to pH 6 to 7 by adding acetic acid dropwise, followed by the addition of water. The precipitated solid is collected by filtration and rinsed with water twice. The wet product is collected and dried in the oven to give 4-phenoxy-N-substituted phthalimide of Formula VIII.

The reduction of step 2 of Scheme IV is run in a mixture of zinc powder and N-alkyl or N-aryl substituted-4-phenoxy-phthalimide of Formula VIII in a sodium hydroxide solution without adding any copper salt, such as copper sulfate, copper nitrate, copper chloride, or copper acetate, or any heavy metal reagents. The concentration of sodium hydroxide solution can be varied from 10% to 40%. The reaction temperature can be in the range of 20° C. to 100° C. As noted above, the composition used in the reduction step is preferably zinc or zinc powder, but can include or be comprised of iron powder, granulated iron, tin powder, granulated tin, a combination of iron powder and ferrous sulfate, a combination of tin powder and stannous chloride.

The ratio of 5-phenoxy-1(3H)-isobenzofuranone of Formula I and its isomer, 6-phenoxy-1(3H)-isobenzofuranone of Formula-Ia, is fa range from 83:17 to 79:21 depending on the substituted R-group present on the N-group of phthalimide.

The purification of the product 5-phenoxy-1(3H)-isobenzofuranone of Formula-I can be effected by three methods: (1) two slurries (a first slurry followed by a second slurry), (2) one slurry and one recrystallization (a slurry and then a recrystallization or a recrystallization and then a slurry) and (3) two recrystallizations (a first recrystallization followed by a second recrystallization).

The purity of the product, 5-phenoxy-1(3H)-isobenzofuranone of Formula I is in the range of 97.0%-99.8%. The undesired regioisomer, 6-phenoxy-1(3H)-isobenzofuranone (Formula Ia) has not been previously reported.

The recovered alkyl amine or aryl amine such as Formula IX, can be re-used as a reactant in the preparation of N-substituted-4-nitro-phthalimide of Formula VII.

Methods for preparing an N-substituted-phthalimide have been previously reported, for example by Foitzik, R. C., et al, (Australian J. of Chem., (2008) 61 (3), 168-171), Navakovski, K., et al. (Bioorganic & Medicinal Chem., (2011) 19 (14): 4295-4306), and Lu, N., et al. (Beilstein J. of Organic Chem., (2012) 8: 192-200), but, the reactive substance in the previously reported methods has no substituted group on 4-position. Thus the present disclosure provides a method for preparing an N-substituted phthalimide having a substituted group at the 4-position. The present disclosure also provides N-substituted phthalimides having a substituted group at the 4-position, such as compounds of Formula VIII, as useful intermediates for the preparation of a compound of Formula I.

SPECIFIC EMBODIMENTS

Embodiment 1. A process for the preparation of 5-phenoxy-1(3H)-isobenzofuranone of Formula I

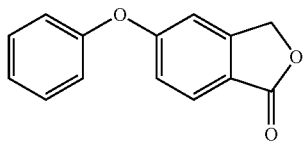

Formula I

The process comprises:

(a) treating N-substituted-4-nitro-phthalimide of Formula VII

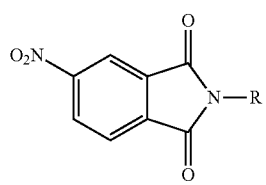

Formula VII where R is optionally substituted $C_1$-$C_8$alkyl or optionally substituted (aryl)$C_0$-$C_4$alkyl, with sodium or potassium phenoxide to form N-substituted-4-phenoxy-phthalimide of Formula VIII. In certain embodiments the groups that can substitute the $C_1$-$C_8$alkyl or (aryl)$C_0$-$C_4$alkyl include halogen, hydroxyl, cyano, nitro, —CONH$_2$, amino, $C_1$-$C_6$alkyl (in which a —CH$_2$— group may be replaced by —O—, —S—, —NH—, or —N($C_1$-$C_6$alkyl)-), $C_1$-$C_2$haloalkyl, or $C_1$-$C_2$haloalkoxy. In certain embodiments R is unsubstituted $C_1$-$C_8$alkyl or unsubstituted (aryl)$C_0$-$C_4$alkyl. For example R can be methyl, ethyl, or benzyl.

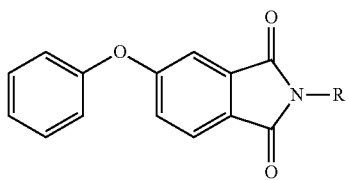

Formula VIII (b) treating the N-substituted 4-phenoxy-phthalimide of Formula VIII with zinc in the presence of a base to give 5-phenoxy-1(3H)-isobenzofuranone of Formula I, its isomer of 6-phenoxy-1 (3H)-isobenzofuranone of Formula Ia, and alkyl amine or aryl amine NH$_2$R (Formula IX);

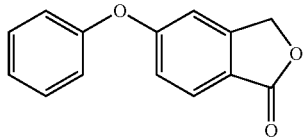

Formula I

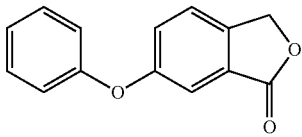

Formula Ia (c) isolating the 5-phenoxy-1(3H)-isobenzofuranone (Formula I) from the 6-phenoxy-1(3H)-isobenzofuranone (Formula Ia).

The base in step (b) of this embodiment may be any base capable of effecting the zinc reduction of Formula VIII to Formula I and Ia. For example the base an alkali metal hydroxide such as sodium hydroxide or potassium hydroxide. The base may be in an aqueous solution.

Embodiment 2. The process of embodiment 1, additionally comprising the step of (d) separating the alkyl amine or aryl amine NH$_2$R (Formula IX) from the 5-phenoxy-1(3H)-isobenzofuranone (Formula I) and the 6-phenoxy-1(3H)-isobenzofuranone (Formula Ia) and reacting the Formula IX with 5-nitroisobenzofuran-1,3-dione (Formula X) to prepare the N-substituted-4-nitro-phthalimide of Formula VII Formula VII Embodiment 3. The process of embodiment 1, wherein R is selected from $C_1$-$C_8$alkyl, phenyl, substituted phenyl, benzyl, or substituted benzyl.

Embodiment 4. The process of embodiment 1, wherein the sodium phenoxide or potassium phenoxide is anhydrous sodium or anhydrous potassium phenoxide, and the anhydrous sodium or anhydrous potassium phenoxide is formed in situ and reacted with the N-substituted-4-nitro-phthalimide of Formula VII to form the N-substituted-4-phenoxy-phthalimide of Formula VIII in a one pot reaction.

Embodiment 5. The process of the preceding embodiment, wherein the sodium or potassium phenoxide is prepared by azeotropic distillation.

Embodiment 6. The process of the preceding embodiment, wherein the sodium or potassium phenoxide is prepared from a solution of 10-40% sodium or potassium hydroxide aqueous solution and a non-aqueous solvent, wherein the solvent is selected from toluene, xylene, trimethylbenzene, heptane, octane, petroleum ether, chlorobenzene or 1,2-dichloroethane.

Embodiment 7. The process of embodiment 1, wherein the base in (b) is a basic aqueous solution and the N-substituted 4-phenoxy-phthalimide of Formula VIII is treated with zinc in the basic aqueous solution.

Embodiment 8. The process of the preceding embodiment, wherein the basic aqueous solution is a sodium hydroxide aqueous solution or a potassium hydroxide aqueous solution.

Embodiment 9. The process of embodiment 8, wherein the concentration of sodium hydroxide or potassium hydroxide in the basic aqueous solution is from 1 to 40%.

Embodiment 10. The process any preceding embodiment, wherein the treating the N-substituted 4-phenoxy-phthalimide of Formula VIII with zinc of (b) is performed at a temperature of from 5 to100° C.

Embodiment 11. The process of any preceding embodiment, wherein the isolation of the 5-phenoxy-1(3H)-isobenzofuranone (Formula I) from the 6-phenoxy-1(3H)-isobenzofuranone (Formula IA) is effected by recrystallization, slurry, or a combination of recrystallization and slurry.

Embodiment 12. The process of the preceding embodiment, wherein the recrystallization or slurry is performed in an alcohol selected from methanol, ethanol, propanol, and butanol, the alcohol containing from 0 to50% water, acetone, acetone/water, butanone, alkyl acetate, acetonitrile, acetonitrile/water, MTBE, THF, THF/water, DMF, DMF/water, NMP or a mixture of any of the foregoing.

Embodiment 13. The process of any preceding embodiment, wherein NH$_2$R (Formula IX) is an alkyl amine selected from methyl amine, ethyl amine, propylamine, isopropyl amine, butyl amine, isobutyl amine, t-butylamine, unsubstituted phenyl amine, substituted phenyl amine, unsubstituted benzyl amine, and substituted benzyl amine.

Embodiment 14. A process for preparing a compound of Formula VIII, comprising of treating N-substituted-4-nitro-phthalimide of Formula VII

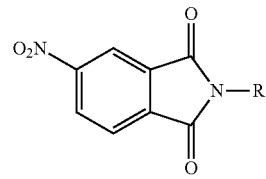

Formula VII where R is substituted or unsubstituted C$_1$-C$_8$alkyl or substituted or unsubstituted (aryl)C$_0$-C$_4$alkyl with sodium or potassium phenoxide to form N-substituted-4-phenoxy-phthalimide of Formula VIII;

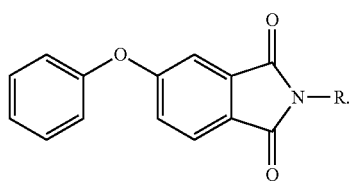

Formula VIII

In certain embodiments R is unsubstituted C$_1$-C$_8$alkyl or unsubstituted (aryl)C$_0$-C$_4$alkyl.

Embodiment 15. The process of the preceding embodiment, wherein R is selected from C$_1$-C$_8$alkyl, phenyl, substituted phenyl, benzyl, or substituted benzyl.

Embodiment 16. The process of embodiment 14 or 15, wherein the sodium or potassium phenoxide is anhydrous sodium or potassium phenoxide, and the anhydrous sodium or potassium phenoxide is formed and reacted with N-substituted-4-nitro-phthalimide of Formula VII to form the N-substituted-4-phenoxy-phthalimide of Formula VIII in a one pot reaction.

Embodiment 17. A process for preparing a compound of Formula I, comprising

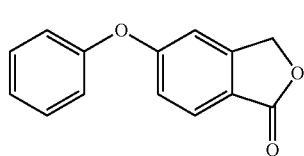

Formula I (1) treating the N-substituted 4-phenoxy-phthalimide of Formula VIII, where R is substituted or unsubstituted C$_1$-C$_8$alkyl or substituted or unsubstituted (aryl)C$_0$-C$_4$alkyl, with zinc in the presence of a base to give 5-phenoxy-1 (3H)-isobenzofuranone of Formula I, its isomer of 6-phenoxy-1 (3H)-isobenzofuranone of Formula Ia, and alkyl amine or aryl amine NH$_2$R (Formula IX);

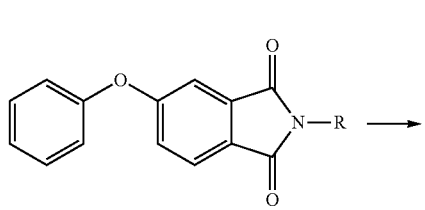

Formula VIII

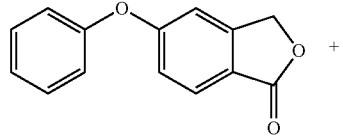

Formula I

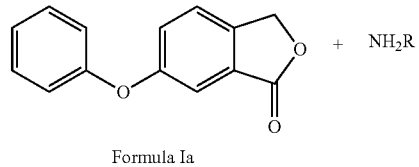

Formula Ia (2) isolating the 5-phenoxy-1(3H)-isobenzofuranone (Formula I) from the 6-phenoxy-1(3H)-isobenzofuranone (Formula Ia). In certain embodiments R is unsubstituted C$_1$-C$_8$alkyl or unsubstituted (aryl)C$_0$-C$_4$alkyl.

Embodiment 18. The process of embodiment 17, wherein the treating the N-substituted 4-phenoxy-phthalimide of Formula VIII with zinc of (b) is performed at a temperature of from 5 to 100° C.

Embodiment 19. A process of preparing a compound of Formula VII,

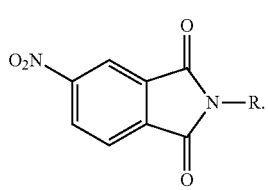

Formula VII comprising of recovering NH$_2$R (Formula IX) from a mixture 5-phenoxy-1(3H)-isobenzofuranone (Formula I) its isomer of 6-phenoxy-1 (3H)-isobenzofuranone (Formula Ia), and alkyl amine or aryl amine NH$_2$R (Formula IX);

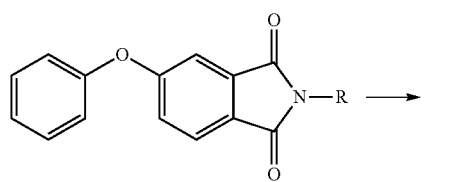

Formula VIII

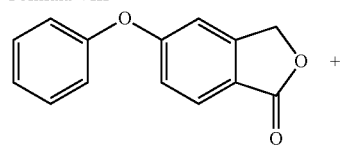

Formula I

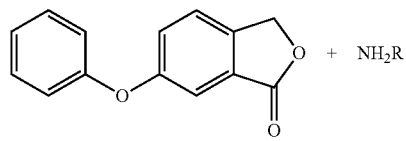

Formula Ia where R is substituted or unsubstituted $C_1$-$C_8$alkyl or substituted or unsubstituted (aryl)$C_0$-$C_4$alkyl, and reacting $NH_2R$ (Formula IX) with 5-nitroisobenzofuran-1,3-dione (Formula X) to provide the compound of Formula VII

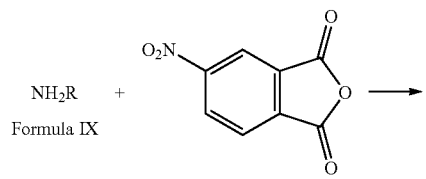

Formula X

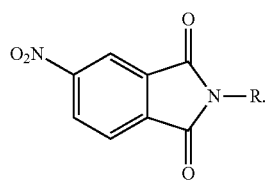

Formula VII

Embodiment 20. The process of the preceding embodiment, where the $NH_2R$ (Formula IX) wherein the $NH_2R$ is recovered from the mixture by extraction into an organic phase of an aqueous-organic extraction liquid.

EXAMPLES

The following abbreviations are used in the examples and claims.
DMF dimethylformamide
DMSO dimethylsulfoxide
MTBE methyl tertiary butyl ether
NMP N-methyl-2-pyrrolidine
PhOH phenol
THF tetrahydrofuran Example 1

Preparation of 4-Phenoxy-N-Methyl Phthalimide of Formula-VIIIB

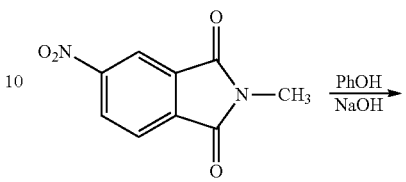

Formula VIIa

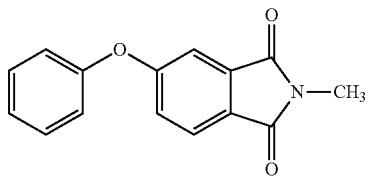

Formula VIIIb

10 N Sodium hydroxide (52.5 ml, 0.525 mole), toluene (206.2 g) and phenol (51.8 g, 0.55 mole) are mixed in a flask, heated to reflux for 60 minutes, then dehydrated by azeotropic distillation to remove water from the system. DMSO (206.2 g) is added to make a solvent exchange. The temperature is kept at 110-115° C. till all of toluene are distilled away. Thereafter the reaction mixture is cooled to 60° C. 4-nitro-N-methyl phthalimide of Formula VIIa (103.1 g, 0.5 mole) is added, and continuously kept running at 60° C. for 6 hours.

The reaction mixture is heated and concentrated to remove most DMSO, then cooled to 20-25° C. The mixture is adjusted pH 6-7 by adding acetic acid dropwise, followed by the addition of water (35 ml). The precipitated solid is collected by filtration, rinsed with water twice (each 300 ml) and filtered. The wet product is collected and dried in the oven to give 121.3 g of 4-phenoxy-N-methyl phthalimide of Formula VIIIb (yield=95%).

Example 2

Preparation of 4-Phenoxy-N-Benzyl Phthalimide of Formula-VIIIA

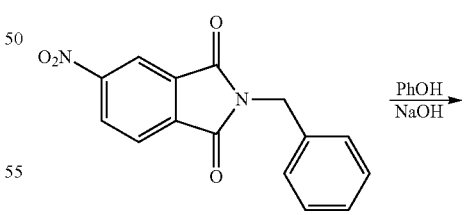

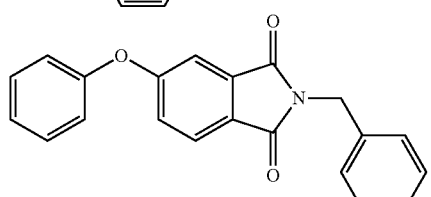

Formula VIIIa

10 N Sodium hydroxide (52.5 ml, 0.525 mole), toluene (206.2 g), and phenol (51.8 g, 0.55 mole) are mixed in a flask, heated to reflux for 30 minutes, then dehydrated by azeotropic distillation to remove water from the system. DMSO (206.2 g) is added to make a solvent exchange. The temperature is kept at 110-115° C. till all of toluene is distilled away. Thereafter the reaction mixture is cooled to 60° C. 4-nitro-N-benzyl phthalimide (141.1 g, 0.5 mole) is added, and continuously kept running at 60° C. for 6 hours.

The reaction mixture is heated and concentrated to remove most of the DMSO, then cooled to 20-25° C. The mixture is adjusted pH 6-7 by adding acetic acid dropwise, followed by the addition of water (350 ml). The precipitated solid is collected by filtration, rinsed with water twice (each 300 ml) and filtered. The wet product is collected and dried in the oven to give 153.1 g of 4-phenoxy-N-benzyl phthalimide of Formula VIIIa (yield=93%).

Example 3

Preparation of 5-Phenoxy-1(3H)-Isobenzofuranone of Formula I and 6-Phenoxy-1(3H)-Isobenzofuranone of Formula IA

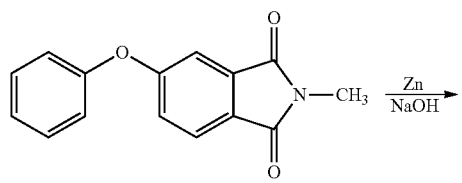

Formula VIIIb

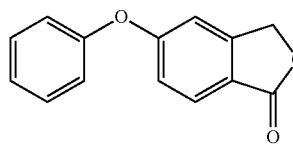

Formula I

Sodium hydroxide (4.0 g, 0.1 mol), water (45.6 g), zinc powder (23.5 g, 0.36 mol), and 4-phenoxy-N-methyl phthalimide (Formula VIIIb, 22.8 g, 0.09 mol) are mixed and heated at reflux for 6 hours. The reaction mixture is cooled to 60° C. Toluene (45.6 g) is added, and followed by adding 36% hydrochloric acid (145.8 g).

The reaction mixture is heated at reflux for 8 hours, during which zinc powder is dissolved completely. Organic layer is separated and washed with water twice (22.8 g each) after the reaction mixture was cooled to 60° C., then concentrated to give the crude mixture of 5-phenoxy-1(3H)-isobenzofuranone of Formula I and 6-phenoxy-1(3H)-isobenzofuranone of Formula Ia (18.3 g, the isomer ratio=83:17, the crude yield: 90%.)

Example 4

Preparation of 5-Phenotype-1(3H)-Isobenofuranone of Formula I and 6-Phenoxy-1(3H)-Isobenzofuranone of Formula IA

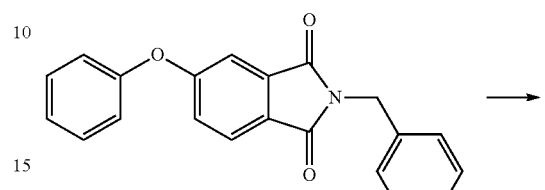

Formula VIIIa

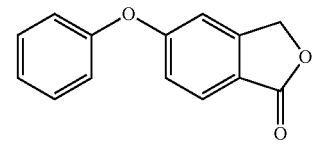

Formula I

Sodium hydroxide (7.7 g, 0.19 mol), water (105.2 g), zinc powder (20.9 g, 0.32 mol), and 4-phenoxy-N-benzyl phthalimide (Formula VIIIa, 26.3 g, 0.08 mol) are mixed and heated at reflux for 6 hours. The reaction mixture is cooled to 5° C. and filtered. The cake is rinsed with water twice (52.5 g each). The filtrate and the rinsed water are combined and transferred slowly into a mixture of 36% hydrochloric acid (40.5 g, 0.4 mole) and 1,2-dichloroethane (65.8 g). The reaction mixture is heated at reflux for 5 hours. The organic layer is separated and washed with water (twice, each 52.5 g) after the reaction mixture was cooled to room temperature, then concentrated to give the crude mixture of 5-phenoxy-1(3H)-isobenzofuranone (Formula I) and 6-phenoxy-1(3H)-isobenzofuranone (Formula Ia) (14.9 g, the isomer ratio=79:21, crude yield: 82%)

Example 5

Recovery and Reuse of Benzylamine to Prepare 4-Nitro-N-Benzyl Phthalimide Of Formula VII ($R^1$=H)

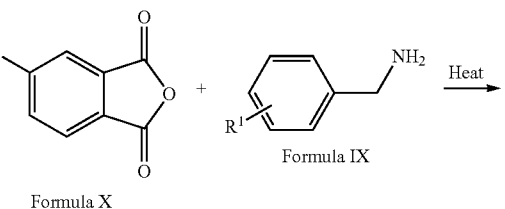

Formula X    Formula IX

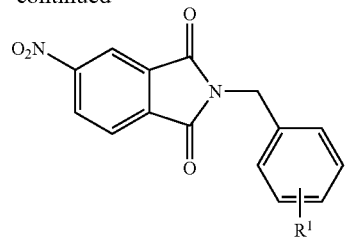

Formula VII

The separated aqueous phase containing benzylamine hydrochloric salt and inorganic salts is basified to pH=11-12 by adding 30% sodium hydroxide aqueous solution and then concentrating to dryness. Dichloromethane (80 ml) is added to dissolve benzylamine. The solvent is evaporated to give benzylamine. 4-nitrophthalic anhydride of Formula X (15.5 g, 0.08 mol) and benzylamine (Formula IX) (8.6 g, 0.08 mol) are mixed in acetic acid (80 ml), and heated to reflux for 3 hours. The reaction is checked by TLC (ethyl acetate/hexane=1:1) until the starting materials have disappeared. The crude product of Formula VII ($R^1$=H) (22.1 g, yield=98%) is obtained after acetic anhydride and acetic acid are distilled away, and can be directly used for next step.

Example 6

Purification of Crude
5-Phenotype-1(3H)-Isobenzofuranone of Formula I
By Slurry Twice in Methanol The mixed products of 5-phenotype-1(3H)-isobenofuranone of Formula I and 6-phenotype-1(3H)-isobenzofuranone of Formula Ia (10 g, the isomer ratio=83:17) are mixed with methanol (45 ml), heated at 60° C. for 30 minutes, cooled to 20° C. and filtered. The collected wet solid is put back into flask and heated with 25 ml of methanol at 60° C. for 30 minutes, cooled to 10° C. and filtered. The desired product of 5-phenotype-1(3H)-isobenzofuranone of Formula I is 61.8 g (yield=61.8%) with a purity of 97.0%.

Example 7

Purification of Crude
5-Phenotype-1(3H)-Isobenzofuranone of Formula-I
By Recrystallization Twice From Methanol The mixed products of 5-phenotype-1(3H)-isobenzofuranone of Formula I and 6-phenotype-1(3H)-isobenzofuranone of Formula Ia (20 g, the isomer ratio=83:17) is mixed with methanol (160 ml), heated at 60° C. to form a clear solution, cooled to 5-10° C. and filtered. The collected wet solid is put back into flask and heated with 160 ml of methanol at 60° C. to form a solution, cooled to 5° C., filtered and dried. The desired product of 5-phenotype-1(3H)-isobenzofuranone of Formula I is 8.0 g (yield=40%) with a purity of 99.7%.

Example 8

Purification of Crude
5-Phenotype-1(3H)-Isobenzofuranone Of Formula I
By One Slurry and One Recrystallization From Methanol The mixed products of 5-phenotype-1(3H)-isobenzofuranone of Formula I and 6-phenotype-1(3H)-isobenzofuranone of Formula Ia (20 g, the isomer ratio=83:17) is mixed with 95% ethanol (60 ml), heated and slurred at 60° C. for 30 minutes, cooled to 5-10° C. and filtered. The collected wet solid is put back into a flask and heated with 160 ml of 95% ethanol at 60° C. to form a solution, cooled to 5° C., filtered, and dried. The desired product of 5-phenotype-1(3H)-isobenofuranone of Formula-I is 8.1g (yield=41%) with a purity of 97.2%.

Example 9

Purification of Crude
5-Phenoxy-1(3H)-Isobenzofuranone of Formula I
By Recrystallization From Toluene The crude mixture of 5-phenoxy-1(3H)-isobenzofuranone and 6-phenoxy-1(3H)-isobenzofuranone (10 g, the isomer ratio=83:17) was mixed with toluene (30 g), heated at 80° C. for 30 minutes, cooled to 10° C. and filtered. The collected wet solid was mixed with toluene (20 g), heated at 80° C. for 30 minutes, cooled to 10° C. and filtered. The collected wet solid was dried in the oven to give desired product of 5-phenoxy-1(3H)-isobenzofuranone (4.6 g, purification yield: 46%) with a purity of 99.3%.

Example 10

Purification of Crude
5-Phenoxy-1(3H)-Isobenzofuranone By
Recrystallization From MTBE The crude mixture of 5-phenoxy-1(3H)-isobenzofuranone (Formula I) and 6-phenoxy-1(3H)-isobenzofuranone (Formula Ia) (10 g, the isomer ratio=83:17) was mixed with MTBE (50 g), heated at 50° C. for 30 minutes, cooled to 10° C. and filtered. The collected wet solid was mixed with MTBE (50 g), heated at 50° C. for 30 minutes, cooled to 10° C. and filtered. The collected wet solid was dried in the oven to give desired product of 5-phenoxy-1(3H)-isobenzofuranone (Formula I) (5.4 g, purification yield: 54%) with a purity of 99.2%.

Example 11

Purification of Crude
5-Phenoxy-1(3H)-Isobenzofuranone By
Recrystallization From Ethyl Acetate The crude mixture of 5-phenoxy-1(3H)-isobenzofuranone (Formula I) and 6-phenoxy-1(3H)-isobenzofuranone (Formula Ia) (10 g, the isomer ratio=83:17) was mixed with ethyl acetate (20 g), heated at 70° C. for 30 minutes, cooled to 10° C. and filtered. The collected wet solid was mixed with ethyl acetate (15 g), heated at 70° C. for 30 minutes, cooled to 10° C. and filtered. The collected wet solid was dried in the oven to give desired product of 5-phenoxy-1(3H)-isobenzofuranone (Formula I) (4.3 g, purification yield: 43%) with a purity of 98.9%.

Example 12

Purification of Crude
5-Phenoxy-1(3H)-Isobenzofuranone (Formula I) By
Recrystallization From 80% Acetone/Water The crude mixture of 5-phenoxy-1(3H)-isobenzofuranone (Formula I) and 6-phenoxy-1(3H)-isobenzofuranone (Formula Ia) (10 g, the isomer ratio=83:17) was mixed with 80% acetone/water (35 g), heated at 50° C. for 30 minutes, cooled to 10° C., and filtered. The collected wet solid was mixed with 80% acetone/water (25 g), heated at 50° C. for 30 minutes, cooled to 10° C. and filtered. The collected wet solid was dried in the oven to give desired product of 5-phenoxy-1(3H)-isobenzofuranone (Formula I) (5.0 g, purification yield: 50%) with a purity of 98.9%.

Example 13

Purification of Crude 5-Phenoxy-1(3H)-Isobenzofuranone By Recrystallization From 80% DMF/Water The crude mixture of 5-phenoxy-1(3H)-isobenzofuranone (Formula I) and 6-phenoxy-1(3H)-isobenzofuranone (Formula Ia) (10 g, the isomer ratio=83:17) was mixed with 80% DMF/water (30 g), heated at 60° C. for 30 minutes, cooled to 10° C. and filtered. The collected wet solid was mixed with 80% DMF/water (25 g), heated at 60° C. for 30 minutes, cooled to 10° C. and filtered. The collected wet solid was dried in the oven to give desired product of 5-phenoxy-1(3H)-isobenzofuranone (Formula I) (5.1 g, purification yield: 51%) with a purity of 99.3%.

Example 14

Purification of Crude 5-Phenoxy-1(3H)-Isobenzofuranone By Recrystallization From 80% Acetonitrile/Water The crude mixture of 5-phenoxy-1(3H)-isobenzofuranone (Formula I) and 6-phenoxy-1(3H)-isobenzofuranone (Formula Ia) (10 g, the isomer ratio=83:17) was mixed with 80% acetonitrile/water (30 g), heated at 60° C. for 30 minutes, cooled to 10° C. and filtered. The collected wet solid was mixed with 80% acetonitrile/water (20 g), heated at 60° C. for 30 minutes, cooled to 10° C. and filtered. The collected wet solid was dried in the oven to give desired product of 5-phenoxy-1(3H)-isobenzofuranone (Formula I) (4.5 g, purification yield: 45%) with a purity of 99.5%.

We claim:

1. A process for the preparation of 5-phenoxy-1(3H)-isobenzofuranone of Formula I

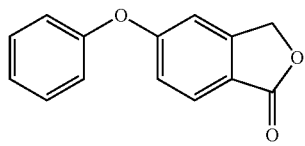

Formula I the process comprising:
(a) treating an N-substituted-4-nitro-phthalimide of Formula VII

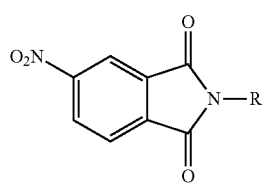

Formula VII where R is substituted or unsubstituted $C_1$-$C_8$alkyl or substituted or unsubstituted (aryl)$C_0$-$C_4$alkyl with sodium or potassium phenoxide to form an N-substituted-4-phenoxy-phthalimide of Formula VIII;

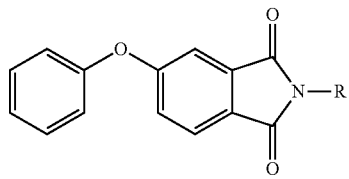

Formula VIII (b) treating the N-substituted 4-phenoxy-phthalimide of Formula VIII with a compound selected from the group consisting of zinc, iron powder, granulated iron, tin powder, granulated tin, a combination of iron powder and ferrous sulfate, a combination of tin powder and stannous chloride, and combinations thereof, in the presence of a base to give 5-phenoxy-1(3H)-isobenzofuranone of Formula I, its isomer of 6-phenoxy-1(3H)-isobenzofuranone of Formula Ia, and alkyl amine or aryl amine $NH_2R$ (Formula IX);

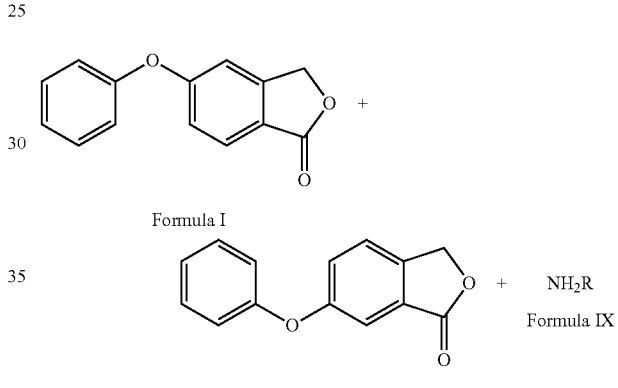

Formula I

Formula Ia

+ $NH_2R$

Formula IX (c) isolating the 5-phenoxy-1(3H)-isobenzofuranone (Formula I) from the 6-phenoxy-1(3H)-isobenzofuranone (Formula Ia).

2. The process of claim 1, additionally comprising the step of
(d) separating the alkyl amine or aryl amine $NH_2R$ (Formula IX) from the 5-phenoxy-1(3H)-isobenzofuranone (Formula I) and the 6-phenoxy-1(3H)-isobenzofuranone (Formula Ia) and reacting the alkyl amine or aryl amine $NH_2R$ (Formula IX) with 5-nitroisobenzofuran-1,3-dione (Formula X) to prepare the N-substituted-4-nitro-phthalimide of Formula VII

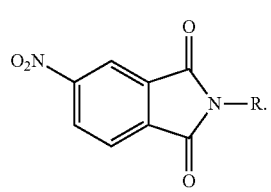

Formula VII

3. The process of claim 1, wherein R is selected from $C_1$-$C_8$alkyl, phenyl, substituted phenyl, benzyl, or substituted benzyl.

4. The process of claim 1, wherein the sodium phenoxide or potassium phenoxide is anhydrous sodium or anhydrous potassium phenoxide, and the anhydrous sodium or anhydrous potassium phenoxide is formed in situ and reacted with the N-substituted-4-nitro-phthalimide of Formula VII to form the N-substituted-4-phenoxy-phthalimide of Formula VIII in a one pot reaction.

5. The process of claim 4, wherein the anhydrous sodium phenoxide or the anhydrous potassium phenoxide is prepared by azeotropic distillation.

6. The process of claim 5, wherein the anhydrous sodium phenoxide or anhydrous potassium phenoxide is prepared from a solution of 10-40% sodium or potassium hydroxide aqueous solution and a non-aqueous solvent, wherein the solvent is selected from toluene, xylene, trimethylbenzene, heptane, octane, petroleum ether, chlorobenzene or 1,2-dichloroethane.

7. The process of claim 1, wherein the base in (b) is a basic aqueous solution, and the N-substituted 4-phenoxy-phthalimide of Formula VIII is treated with zinc in the basic aqueous solution.

8. The process of claim 7, wherein the basic aqueous solution is a sodium hydroxide aqueous solution or a potassium hydroxide aqueous solution.

9. The process of claim 8, wherein the concentration of sodium hydroxide or potassium hydroxide in the basic aqueous solution is from 1 to 40%.

10. The process of claim 1, wherein treating the N-substituted 4-phenoxy-phthalimide of Formula VIII is step (b) is with zinc and is performed at a temperature of from 5 to 100° C.

11. The process of claim 1, wherein the isolation of the 5-phenoxy-1(3H)-isobenofuranone (Formula I) from the 6-phenoxy-1(3H)-isobenzofuranone (Formula Ia) is effected by recrystallization, slurry, or a combination of recrystallization and slurry.

12. The process of claim 11, wherein the recrystallization or slurry is performed in an alcohol selected from methanol, ethanol, propanol, and butanol, the alcohol containing from 0 to 50% water, acetone, acetone/water, butanone, alkyl acetate, acetonitrile, acetonitrile/water, MTBE, THF, THF/water, DMF, DMF/water, NMP or a mixture of any of the foregoing.

13. The process of claim 2, wherein $NH_2R$ (Formula IX) is an alkyl amine or aryl amine selected from methyl amine, ethyl amine, propylamine, isopropyl amine, butyl amine, isobutyl amine, t-butylamine, unsubstituted phenyl amine, substituted phenyl amine, unsubstituted benzyl amine, and substituted benzyl amine.

14. A process for preparing a compound of Formula I, comprising

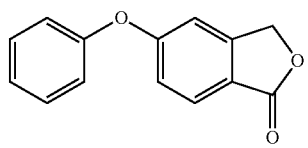

Formula I (1) treating the N-substituted 4-phenoxy-phthalimide of Formula VIII, where R is substituted or unsubstituted $C_1$-$C_8$alkyl or substituted or unsubstituted (aryl)$C_0$-$C_4$alkyl, with a composition selected from the group consisting of zinc, iron powder, granulated iron, tin powder, granulated tin, a combination of iron powder and ferrous sulfate, a combination of tin powder and stannous chloride, and combinations thereof, in the presence of a base to give 5-phenoxy-1(3H)-isobenzofuranone of Formula I, its isomer, 6-phenoxy-1 (3H)-isobenzofuranone of Formula Ia, and an alkyl amine or aryl amine $NH_2R$ (Formula IX);

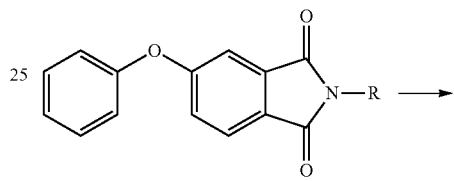

Formula VIII

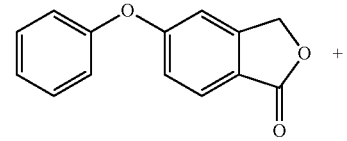

Formula I

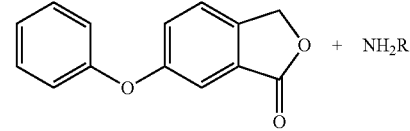

Formula Ia (2) isolating the 5-phenoxy-1(3H)-isobenzofuranone (Formula I) from the 6-phenoxy-1(3H)-isobenzofuranone (Formula Ia).

15. The process of claim 14, wherein the treating the N-substituted 4-phenoxy-phthalimide of Formula VIII with zinc of (b) is performed at a temperature of from 5 to 100° C.

* * * * *